US012702619B2

(12) United States Patent
Johnson

(10) Patent No.: US 12,702,619 B2
(45) Date of Patent: Aug. 11, 2026

(54) STEAM TENT SYSTEM AND METHOD

(71) Applicant: PinTech LLC, Aurora, CO (US)

(72) Inventor: Vincent Johnson, Aurora, CO (US)

(73) Assignee: PinTech LLC, Aurora, CO (US)

( * ) Notice: Subject to any disclaimer, the term of this patent is extended or adjusted under 35 U.S.C. 154(b) by 702 days.

(21) Appl. No.: 18/053,366

(22) Filed: Nov. 7, 2022

(65) Prior Publication Data

US 2023/0142810 A1 May 11, 2023

Related U.S. Application Data

(60) Provisional application No. 63/276,174, filed on Nov. 5, 2021.

(51) Int. Cl.
*A61H 33/00* (2006.01)
*A61H 23/02* (2006.01)
(Continued)

(52) U.S. Cl.
CPC ....... *A61H 33/005* (2013.01); *A61H 23/0236* (2013.01); *A61H 33/066* (2013.01); *A61N 5/0613* (2013.01); *A61N 5/0616* (2013.01); *A61H 2033/0004* (2013.01); *A61H 2033/0083* (2013.01); *A61H 2033/068* (2013.01); *A61H 2201/10* (2013.01); *A61H 2201/5048* (2013.01); *A61N 2005/0626* (2013.01); *A61N 2005/0636* (2013.01); *A61N 2005/0651* (2013.01); *A61N 2005/0659* (2013.01); *A61N 2005/0663* (2013.01); *E04H 15/12* (2013.01); *E04H 15/54* (2013.01)

(58) Field of Classification Search
None
See application file for complete search history.

(56) References Cited

U.S. PATENT DOCUMENTS 4,130,120 A * 12/1978 Kohler, Jr. ........... A61N 5/0614 607/80
6,500,197 B1 * 12/2002 Buesselmann ....... A61H 33/063 607/83

(Continued)

FOREIGN PATENT DOCUMENTS

AU 2016201260 A1 * 9/2017
EP 2353478 A2 * 8/2011 ............... A47K 3/28

(Continued)

OTHER PUBLICATIONS

"Mirzaei, Royalty-Free 432Hz Music, Jun. 16, 2021, Meditation Music Library by Music of Wisdom, https://meditationmusiclibrary.com/blogs/wednesday-wisdom-blog/royalty-free-432hz-music?srsltid=AfmBOooGHHGzQ0E6os874aG0f-iTF1zqa4EwEqqrLrxV3MBtmvNyR7t2" (Year: 2021).*

*Primary Examiner* — Michael T. Holtzclaw
(74) *Attorney, Agent, or Firm* — Holland & Hart LLP

(57) ABSTRACT

The disclosed technology includes devices, systems, and methods of fabricating and using a therapeutic tent to non-invasively treat burns, respiratory illnesses, muscle issues, and various other illnesses and physical, psychological, and emotional conditions. In some implementations, a disclosed system includes a tent, a steam source configured to supply an interior of the tent with steam, and a light source configured to illuminate the tent. The tent, the steam, and the light source are configured to treat a condition.

19 Claims, 13 Drawing Sheets

(51) Int. Cl.

| | |
|---|---|
| ***A61H 33/06*** | (2006.01) |
| ***A61N 5/06*** | (2006.01) |
| ***E04H 15/12*** | (2006.01) |
| ***E04H 15/54*** | (2006.01) |

(56) References Cited

U.S. PATENT DOCUMENTS

| | | | | |
|---|---|---|---|---|
| 2003/0188378 | A1* | 10/2003 | Brunelle | A61H 33/06 4/597 |
| 2004/0260364 | A1* | 12/2004 | Daffer | A61H 9/00 607/81 |
| 2009/0019634 | A1* | 1/2009 | Lipponen | A61H 33/06 4/524 |
| 2010/0017953 | A1* | 1/2010 | O'Keeffe | G06Q 10/0639 219/480 |
| 2010/0204760 | A1* | 8/2010 | Lawliss | A61H 33/066 607/81 |
| 2015/0218784 | A1* | 8/2015 | Mazz | E03C 1/055 4/597 |
| 2017/0080246 | A1* | 3/2017 | Knight | A61M 21/02 |
| 2018/0360649 | A1* | 12/2018 | Daffer | A63B 71/04 |
| 2020/0008996 | A1* | 1/2020 | Zack | A61N 5/0625 |

FOREIGN PATENT DOCUMENTS

| | | | | |
|---|---|---|---|---|
| RU | 2192235 C2 * | 11/2002 | | |
| WO | WO-2017116077 A1 * | 7/2017 | | H05B 3/12 |

* cited by examiner

STEAM TENT SYSTEM AND METHOD

TECHNICAL FIELD

This application claims the benefit of and priority to U.S. Provisional Patent Application No. 63/276,174, filed Nov. 5, 2021, which is hereby incorporated by reference in its entirety.

TECHNICAL FIELD

This disclosure relates to a steam tent device that can be used with a sound source and a light source to treat various burns, illnesses, diseases, and other medical conditions.

BACKGROUND

Steam bathing is an old practice used by many cultures in different countries. With the growing number of fitness clubs, spas, and wellness centers, steam rooms are commonly used after workouts and in spas for relaxation and recovery. Unfortunately, accessibility to these facilities may be challenging for many people. People either do not have the funds to consistently take advantage of high-quality steam facilities or lack the time to take advantage of a high-quality facility. Even if a person has the time, money, and access to quality steam facilities, the likelihood of feeling comfortable in an environment that is not private can cause anxiety and be counterproductive.

SUMMARY

The disclosed technology is directed to a tent device. In some implementations, the present disclosure includes a tent system, including a tent, a steam source configured to supply an interior of the tent with steam, and a light source configured to illuminate the tent. The tent, the steam, and the source are configured to treat a condition. The tent may be made of hemp. In some implementations, the tent is hermetically sealed. In some implementations, the tent is an anti-microbial environment.

In some implementations, the steam source includes a water tank, a water filler, a pressurized steam generator, a vaporizer, and an overflow tank. The steam source may provide steam in a range of 105-120 degrees Fahrenheit.

In some implementations, the light source is LED/infrared. In some implementations, the tent system further includes a sound source. In some implementations, the sound source is 432 Hz.

In other implementations, wireless technology may be used to control at least one of the steam source, the light source, and the sound source. The tent system may be portable, and in some cases weighs less than 50 lbs.

In some implementations, the present disclosure includes a method for fabricating a tent system, including providing a hermetically sealed tent, implementing a steam source into the hermetically sealed tent, affixing at least one light source into the hermetically sealed tent, and providing a sound source to the hermetically sealed tent. The tent may be made of a variety of materials (e.g., hemp).

In some implementations, a method of using a tent system includes providing a hermetically sealed tent, providing a steam source, providing a light source, providing a sound source, and placing a user inside the hermetically sealed tent, and exposing the user to steam, light, and sound.

In some implementations, a method of treatment of a condition includes providing a hermetically sealed tent, the hermetically sealed tent including a steam source, a light source, and a sound source, determining a first predetermined administration of steam based on the condition, determining a second predetermined administration of light based on the condition, determining a third predetermined administration of sound based on the condition, placing a user inside the hermetically sealed tent, administering the first predetermined administration of the steam to the user, administering the second predetermined administration of the light to the user, and administering the third predetermined administration of the sound to the user.

In some implementations, the determined second predetermined administration of the light is selected from LED/infrared light. In some implementations, red light is selected if the condition includes at least one of muscle, immunological, metabolic, skin, and blood circulation conditions. In some implementations, blue light is selected if the condition includes at least one of skin and fluid conditions. In some implementations, green light is selected if the condition includes skin conditions. In some implementations, the third predetermined administration of the sound is at 432 Hz.

These and various other features and advantages will be apparent from a reading of the following detailed description.

DRAWINGS

Implementations are disclosed in association with the accompanying drawings in which.

Figure 8A:
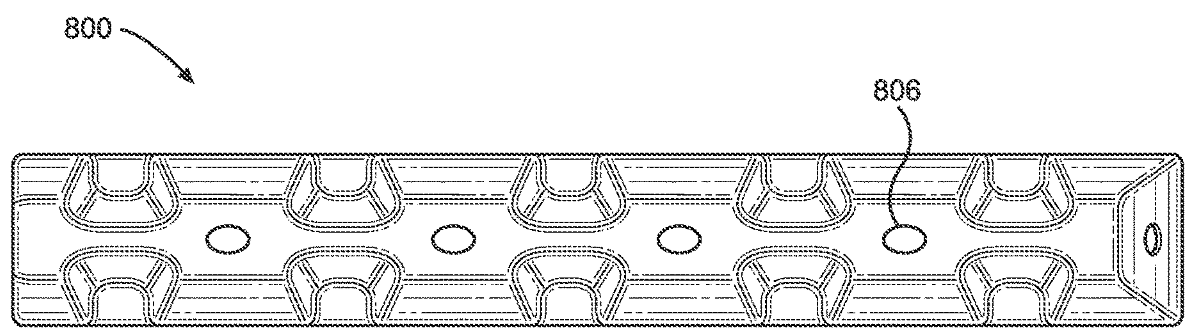
Figure 8B:
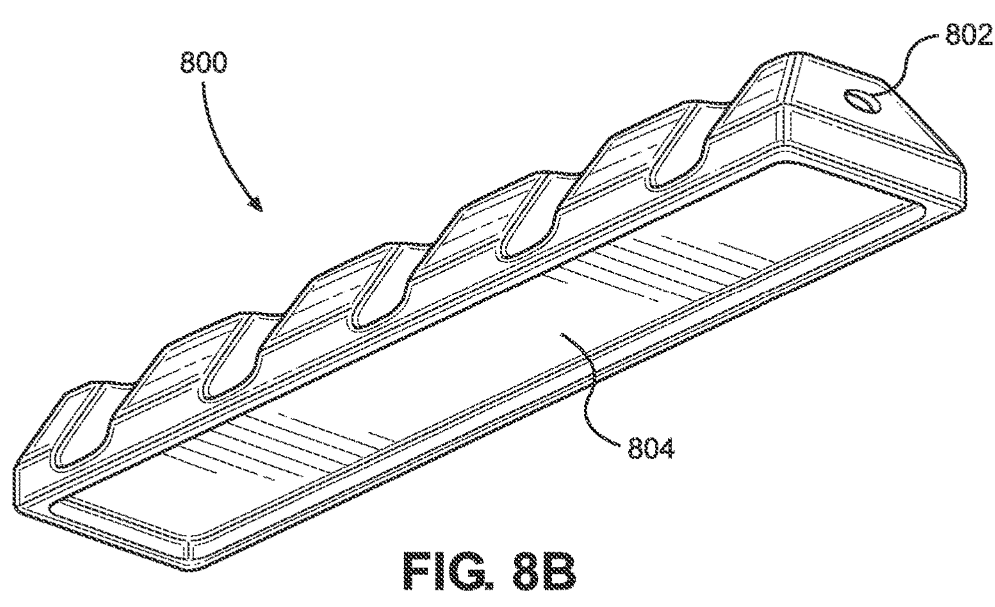
Figure 8C:
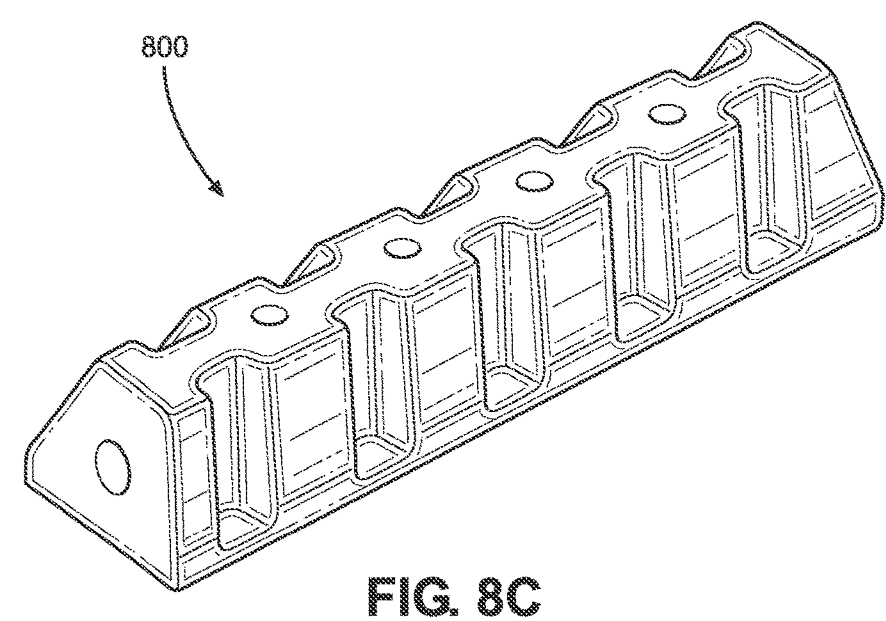

FIG. 8A-C are schematic diagrams of a steam source of a tent system in accordance with aspects in the present disclosure.

Figures 9A, 9B, 9C:
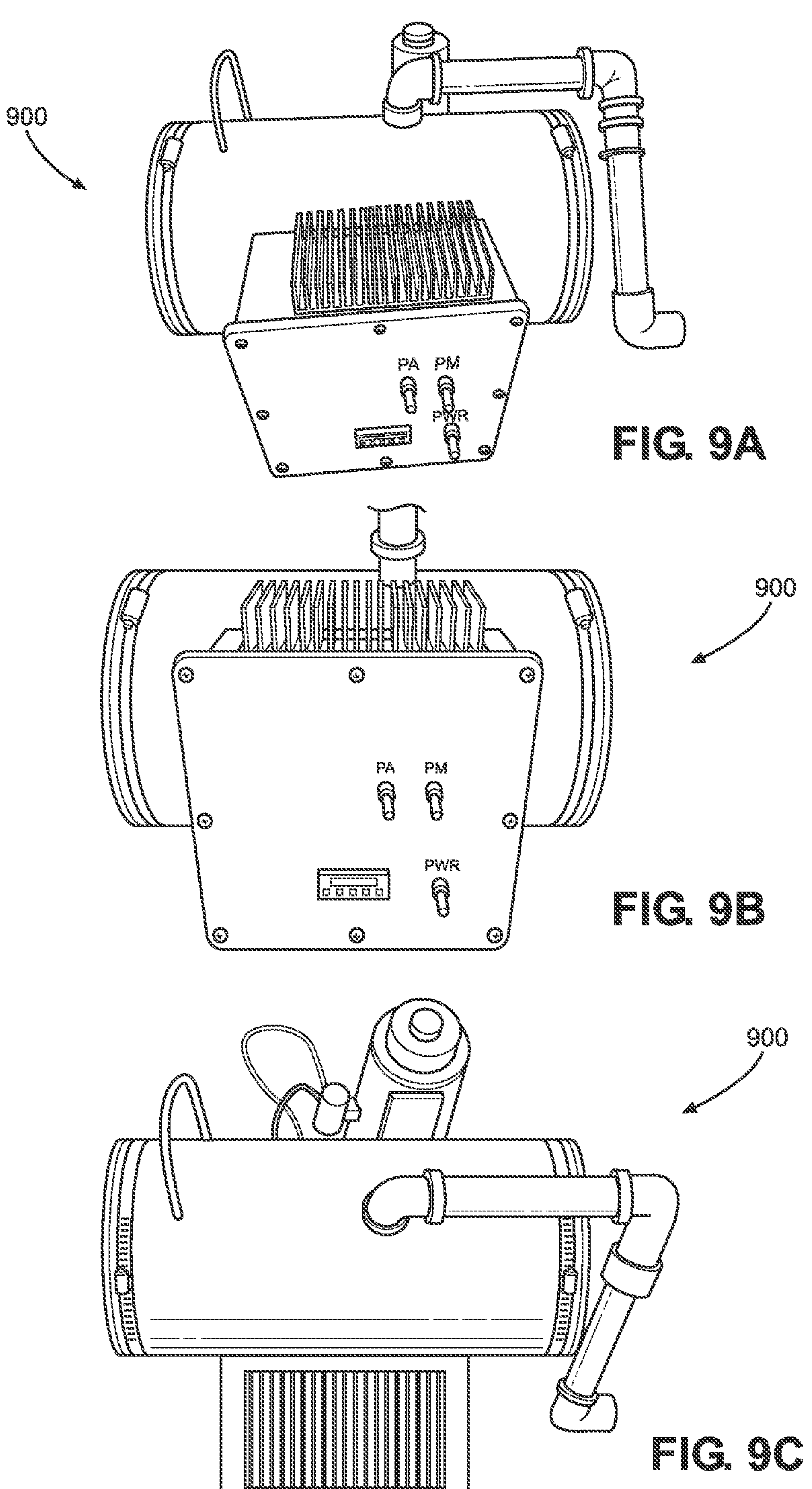

FIG. 9A-C illustrate perspective views of a steam source of a tent system in accordance with aspects in the present disclosure.

Figure 10:
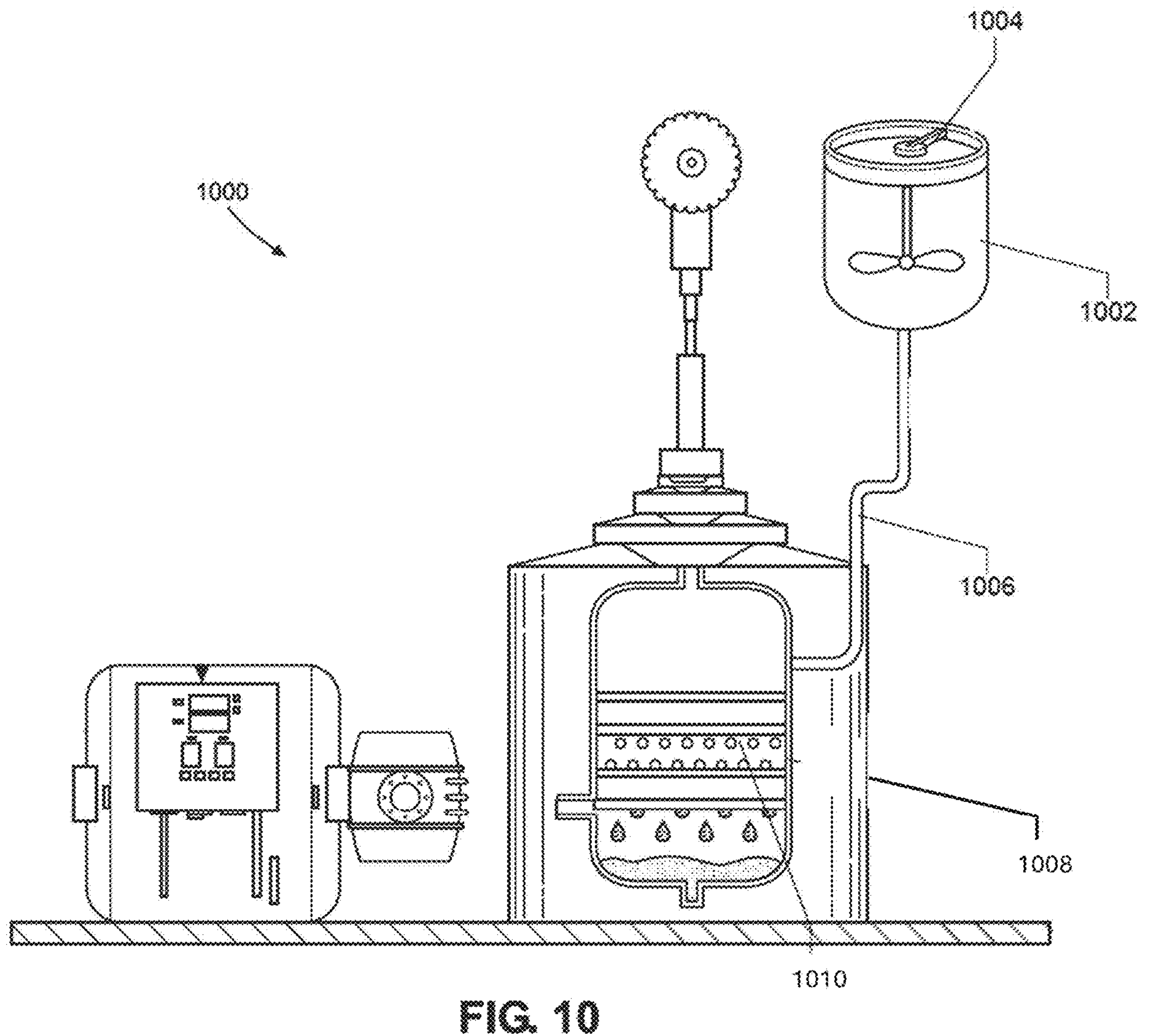

FIG. 10 illustrates a schematic diagram of a steam source in accordance with aspects in the present disclosure.

Figure 11:
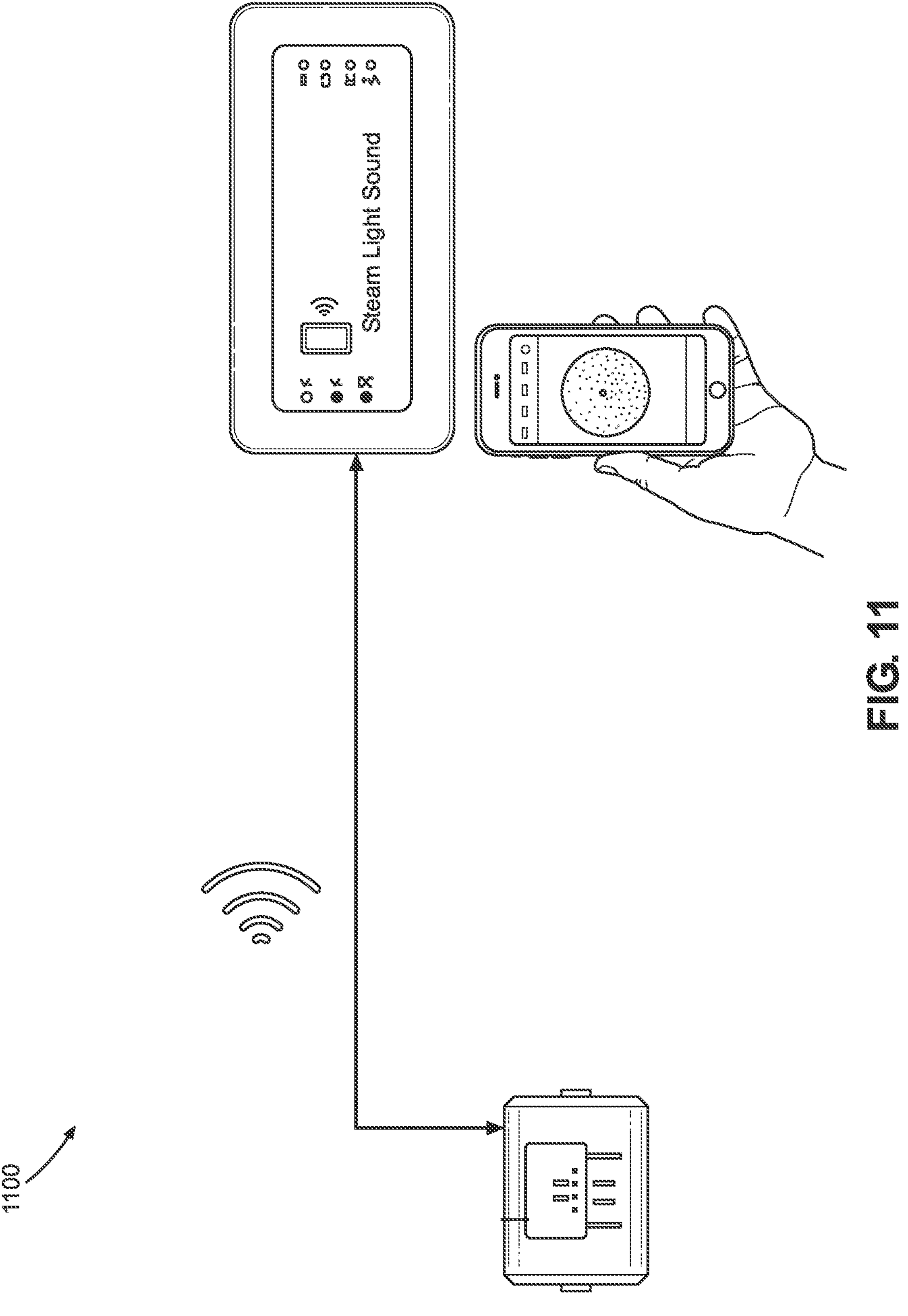

FIG. 11 is a flowchart of an example Bluetooth control system for controlling a tent system in accordance with aspects in the present disclosure.

Figure 12:
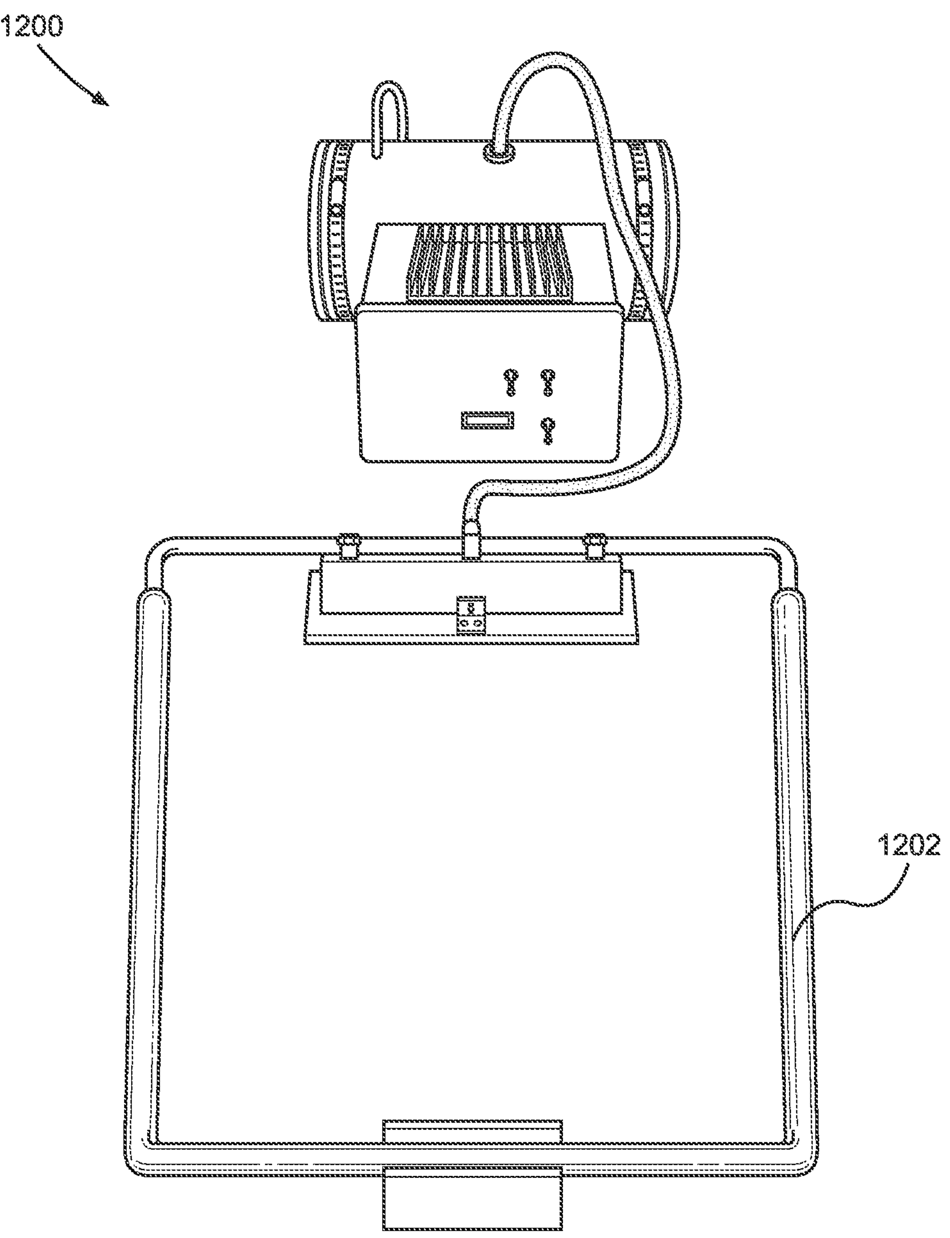

FIG. 12 is a perspective view of a contoured steam dispenser of a tent system in accordance with aspects in the present disclosure.

Figure 13:
Figure 13:
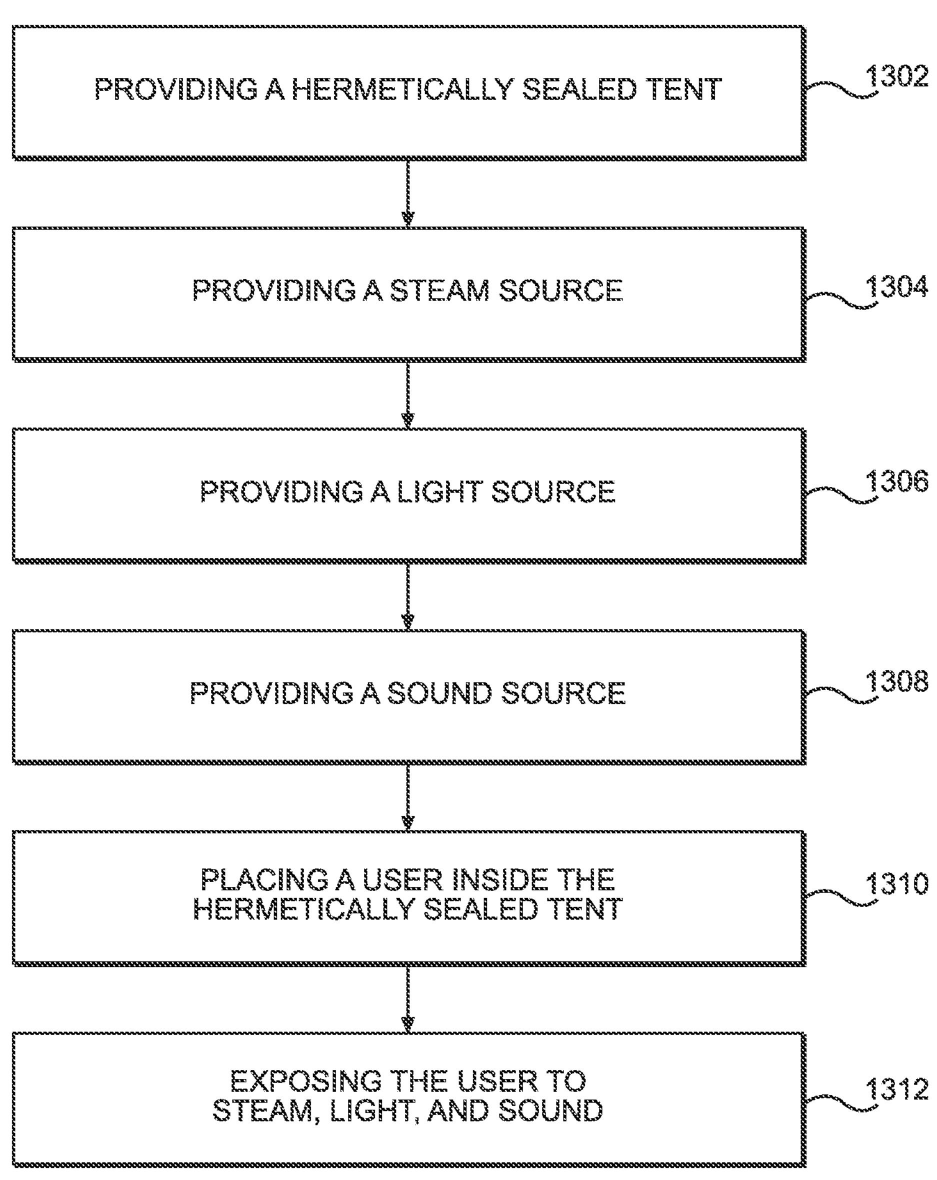

FIG. 13 is a flowchart of example operations for methods for fabricating a tent system in accordance with aspects in the present disclosure.

Figure 14:
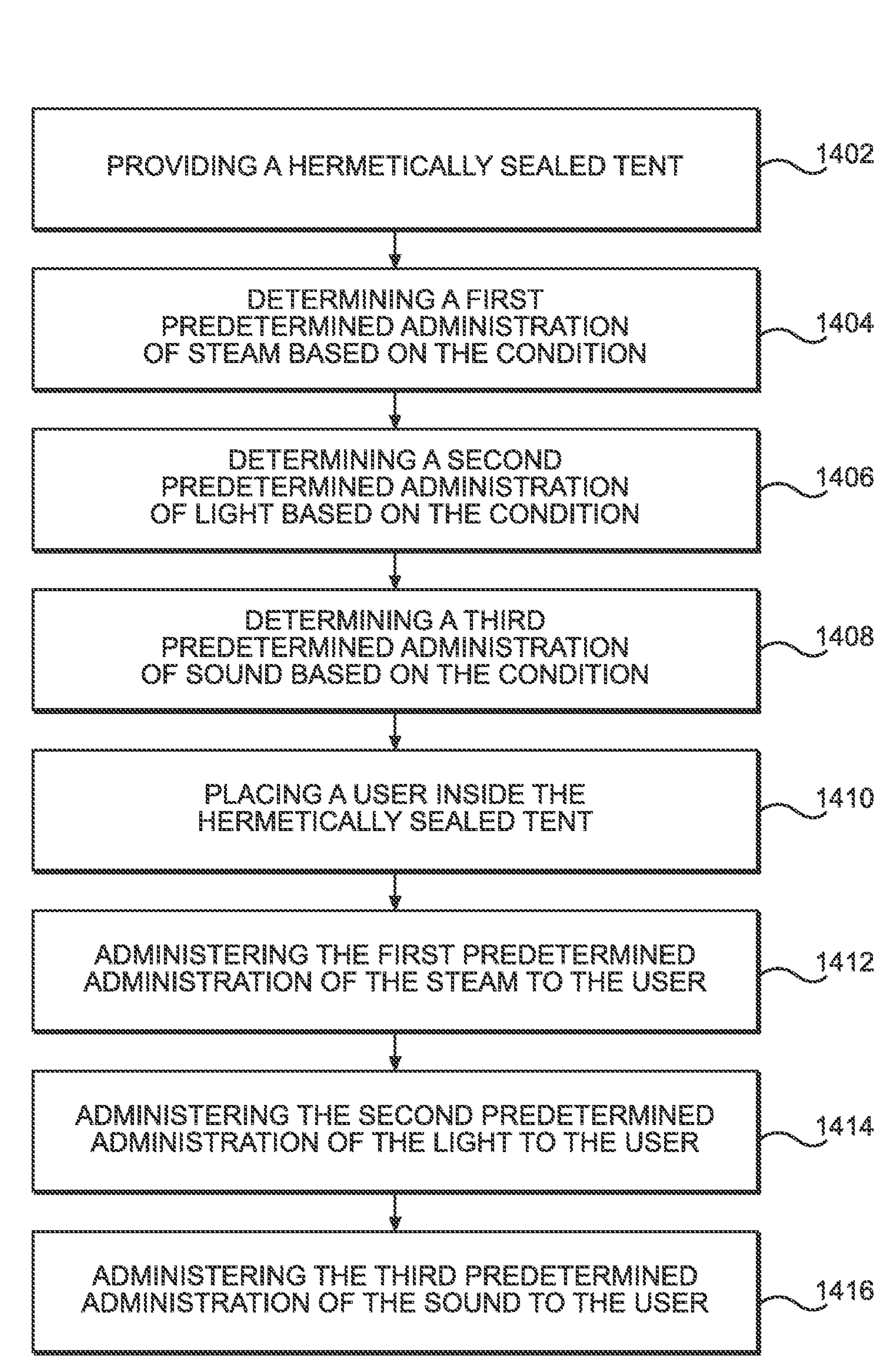

FIG. 14 is a flowchart of example operations for methods for using a tent system in accordance with aspects in the present disclosure.

DETAILED DESCRIPTION

The present disclosure is directed to a therapeutic tent system that includes a tent and combinations of a steam source, a light source, and a sound source.

Conventional steam rooms are rooms at a spa or workout facility and require a user to travel for use. Furthermore, users need to pay for the steam room use. Further yet, while steam itself provides numerous health benefits, there are other components (e.g., light, sound) that can facilitate faster and better treatment and recovery and for more illnesses and conditions.

In accordance with aspects of the present disclosure, to address some of these shortcomings, a mobile, affordable, and convenient tent system is described that may effectively and efficiently treat various physical, psychological, and emotional conditions of a user. The tent system treats users suffering from various conditions, including, but not limited to, PTSD, muscle related injuries, inflammation, circulatory issues, muscle issues, and burn victims.

More specifically, by way of example, the tent system:

1. Improves circulation: Sitting in a steam room may significantly improve cardiovascular health. A study of older individuals showed that moist heat improved circulation, especially in extremities. Improved circulation can lead to lowered blood pressure and a healthier heart. It can also promote healing of broken skin tissue.

2. Lowers blood pressure: Research shows that in a steam room, some individual's bodies release hormones that change their heart rate. One of these hormones, called aldosterone, regulates blood pressure. When aldosterone is released from sitting in the steam room, it can help lower high blood pressure. This is part of the reason that the steam room makes most individuals feel relaxed.

3. Reduces stress: Being in the steam room can also decrease an individual's production of cortisol. Cortisol is the hormone that regulates the level of stress that an individual may feel. When cortisol levels drop, an individual feels more in control and relaxed. Spending a few minutes in a relaxed state not only improves your health, but also helps heal the mind and improves focus.

4. Clears congestion: Steam rooms create an environment that warms the mucous membrane and encourages deep breathing. As a result, using one can help break up congestion inside sinuses and lungs. Steam therapy used for treating colds and sinus infections at home is controversial because of the potential for scalding if used incorrectly. However, steam rooms are relatively safe in comparison, provided there is not overexposure. A study performed on a group of children found that children with respiratory infections recovered more quickly after steam therapy than children who did not use steam therapy.

5. Promotes skin health: Through environmental exposure, toxins can become trapped underneath the skin. Steam rooms help solve that problem by using heat to open up your pores. The warm condensation rinses away the dirt and dead skin that can lead to breakouts. As a result, an individual can have clearer and more even-toned skin from stream room use.

6. Aids in workout recovery: The pain an individual may feel after working out is called delayed onset muscles soreness (DOMS). Professional athletes have known for decades that heat therapy can help them recover from training workouts. Heat can penetrate deep into muscle tissue and help relieve DOMS. A recent study showed that moist heat works as effectively and more quickly than dry heat in muscle recovery.

7. Loosens stiff joints: Warming up before a workout is critical in avoiding injury. Using a steam room as part of a warm-up could help an individual reach maximum mobility during activities such as running, Pilates, and yoga. One study found that when heat was applied to the knee joint before activity, the joint was far more flexible and relaxed. The results showed that heat can help reduce injury before a workout. It was also found that women especially benefited from heat therapy on the knee joint to prevent injury.

8. Burns calories: A steam room or sauna increased heart rate. If you use a steam room after an aerobic workout, the heart rate is already elevated, and the steam room can prolong that elevation. When used correctly, experts note that saunas and steam rooms stimulate the body in ways that typical exercise does not. While weight loss in a steam room is likely water weight, which will need to be replaced by water to avoid dehydration, using steam rooms regularly as a way to burn more calories at the gym may help a diet and exercise routine be more effective.

9. Boosts the immune system: Different forms of hydrotherapy, including steam rooms, are known to boost immunity. Exposing the body to warm water stimulates leukocytes, cells that fight infection. Using steam rooms regularly may provide an immunity boost to the bloodstream that can result in reducing sickness.

10. Treats PTSD: Light therapy is used by some alternative medicine practitioners to treat wounds and pain. The light from the diodes has been shown to boost the output of nitric oxide near where the LEDs are placed, which improves blood flow in that location.

In some implementations, the tent system may be conveniently used in a user's house and may be portable. (e.g., in some cases, less than 50 lbs.). In other implementations, the tent system may weigh as much as 75 lbs. The tent system may be a one-time purchase and available for repeated use.

In some implementations, the tent system may include hemp or other material capable of being hermetically sealed. In some implementations, the tent system may be a non-microbial environment. In some implementations, Bluetooth or other wireless technology may be implemented into the tent system for controlling the tent system, including the steam source, the light source, and the sound source.

In some implementations, the light source may include multiple lights or strips of lights that may be located in various locations in the tent. For example, the light source(s) may be attached hanging from the top of the tent or affixed to the side of the tent. The light source may be attached to the tent by any affixing means (e.g., Velcro, ties, clips, thread, etc.). In other implementations, the light source may be free standing inside the tent.

Definitions

The term "tent" refers to a material, housing, or casing that encloses a user and provides a steam room environment. The components of the tent system may be located inside or outside of the tent. For example, a steam source may be located inside or outside of the tent.

The term "steam source" refers to any machine configured for steam production.

The term "light source" refers to LED/Infrared Light. In some implementations, the light will have the red/green/blue spectral range.

The term "sound source" refers to sounds provided within the tent of the tent system that consists of very specific tones and frequency ranges to promote healing and a sense of well-being. A sound source can be one or more sounds, and can include sounds, songs, rhythms, beats and/or melodies that are configured to promote healing and a sense of well-being.

The terms “individual”, “subject”, “patient”, “person,” “listener,” and “user” are used interchangeably herein and refer to any mammalian subject for whom use of the tent system is desired, particularly humans.

The terms “a”, “an”, and “the” refer to embodiments having plural referents, unless the content clearly dictates otherwise. As used in this specification and the appended claims, the term “or” is generally employed in its sense including “and/or” unless the content clearly dictates otherwise.

All ranges set forth herein in the summary and description of the disclosed technology and the claims include all numbers or values thereabout or therebetween of the numbers of the range. The ranges of the disclosed technology expressly denominate and set forth all integers, decimals and fractional values in the range.

The terms “about” and “approximately” in the context of numerical values and ranges refers to values or ranges that approximate or are close to the recited values or ranges such that the disclosed technology can perform as intended, such as having a desired rate, amount, degree or extent of absorption and desensitization, as is apparent from the teachings contained herein. Thus, this term encompasses values beyond those simply resulting from systematic error. By “substantially,” as recognized by the skilled person, it is meant in this and similar contexts that the products and methods are suitable for their intended purpose. The following description provides specific embodiments. It is to be understood that other embodiments are contemplated and may be made without departing from the scope or spirit of the present invention. The following detailed description, therefore, is not to be taken in a limiting sense. While the present invention is not so limited, an appreciation of various aspects of the invention will be gained through a discussion of the examples provided below.

The term “treating” in its various grammatical forms in relation to the present disclosed technology refers to, depending on context, avoiding, preventing, curing, reversing, attenuating, alleviating, minimizing, suppressing or halting the deleterious effects of a physical, emotional, or psychological condition, illness, disease state, disease progression, disease causative agent or other abnormal or undesired condition, as recognized by the skilled person or a person in need of treatment. In one implementation of the disclosed technology, burns are treated.

Figure 1:
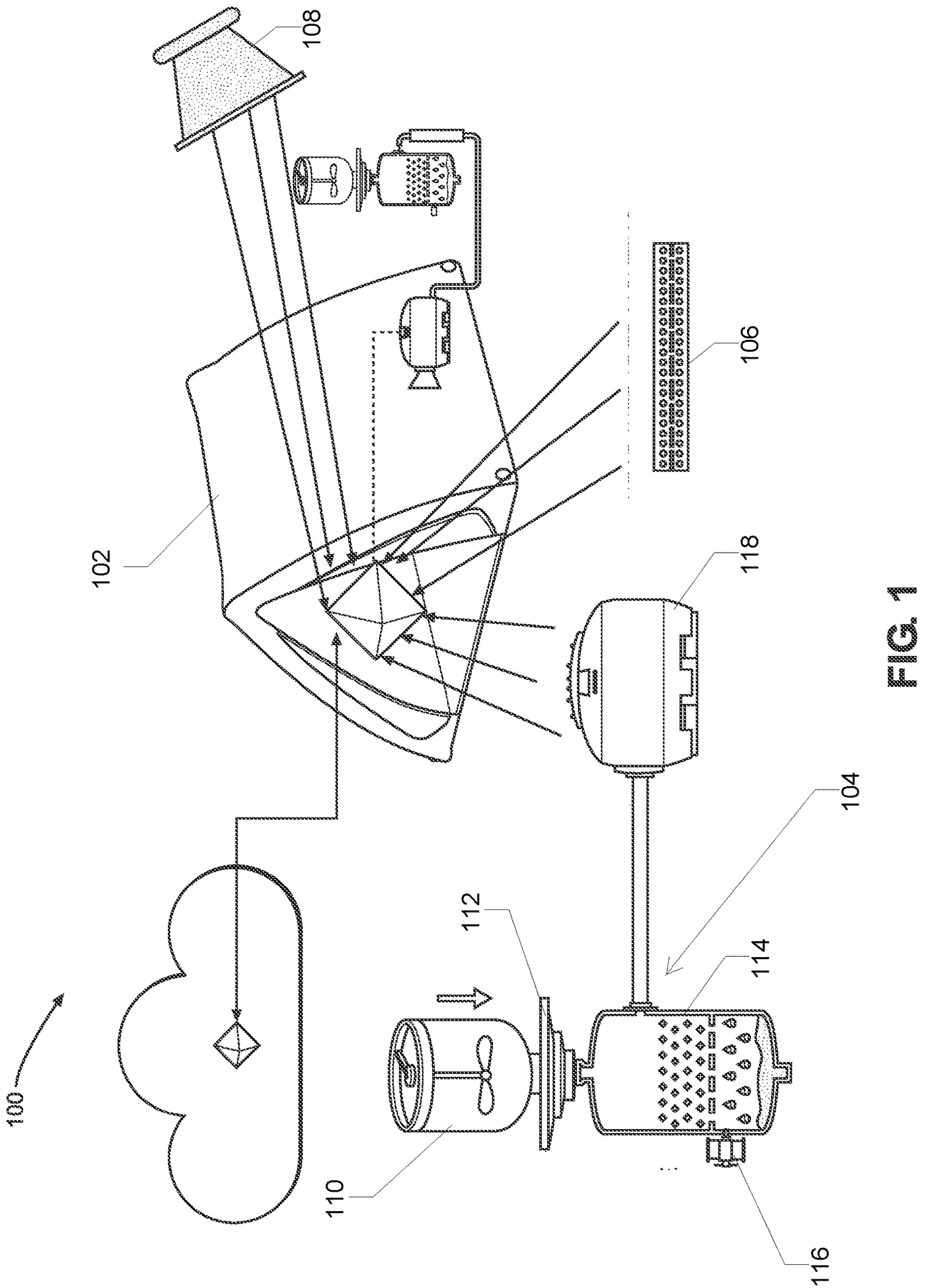
FIG. 1 illustrates a schematic diagram of a tent system in accordance with aspects in the present disclosure.

FIG. 1 illustrates a schematic diagram of a tent system 100 in accordance with aspects in the present disclosure. The tent system 100 includes four main components: a tent 102, a steam source 104, a light source 106, and a sound source 108. In the tent system 100 in FIG. 1, the tent 102 is made of hemp fabric. In other implementations, other fabrics may be used. The tent fabric may be configured to be hermetically sealed and provide an anti-microbial environment.

The steam source 104 shown in FIG. 1 includes a water tank 110 with a filter 112. The water may be placed in the water tank 110 and filtered to a pressurized steam generator 114, which includes a tank release 116. Air and water vapor move to a removable overflow tank 118 and steam is provided into the tent 102.

In one implementation, the steam source 104 may be a Wagner 715 Power Steamer® with a 1-gallon tank and a 1500-Watt heating element that provides up to 70 minutes of steam time from one fill. The unit’s specifications are 120V for the Wagner 715 Power Steamer®, 60 HZ and 1500 W×2 for the heating element. The assembled product dimensions are (L×W×H) 14.00×14.00×14.00 Inches. The mini-max steam temperature is in a range from 102-120 Fahrenheit, and humidity approximately 100. Pre-heating time may take approximately 20 minutes and can vary. In some implementations, the steam source 104 may be adapted for a 110-watt outlet. In other implementations, the steam source may be adapted for two 110-watt outlets. Other steam sources are contemplated.

A light source is located in the tent. In FIG. 1, the light source 106 is near infrared lighting. In other implementations, other light sources may be used.

Different color light may be selected based on the treatment desired for a particular user’s condition. For example, infrared light (850 nm) and red light (660 nm) may be used to penetrate tissue to a depth of about 8-10 mm to help promote blood circulation and the relaxation of muscles, enhance immunity, stimulate metabolism, produce new collagen and provide an overall healthy, radiant and more even toned and younger looking complexion. Infrared light (850 nm) and red light (660 nm) may also be used to increase collagen production fivefold in the skin, triggering repair mechanism and stimulating fibroblast cells and cell growth.

In another example, blue light (415 nm) may be used to improve acne prone skin with its purifying and antibacterial properties. It effectively reduces the amount of fluid in the face and treats sensitive skin to provide a clear complexion.

In another example, green light (525 nm) may be used to reduce pigmentation through penetration into base skin layers, prevents the formation of fleck, gravid and aging pigment to keep skin smooth and bright.

Example optimal light intensity ranges for cells are at color/wavelength 0.1 J/cm$^2$ to 6 J/cm$^2$. Example LED/Lamp side watts are:

1. Time=Dose±(Power density×0.001); and
2. LED Light Colors: Green, Blue, Red, Violet.

Additional guidance for selection of a specific light source used in a particular tent depending on the desired treatment is provided in the following chart: The color of the lighting may be adjusted according to the desired result. For example, red may be selected for younger looking skin and decreased signs of aging including reduction of fine lines and wrinkles by increasing collagen production. Additionally, violet may be selected to increase cell regeneration to cleanse the skin and reduce inflammation. Blue may also be selected to reduce acne and whiten teeth because blue light reduces the bacteria that causes acne and may whiten teeth. Cyan may be selected to smooth skin because it is a smoothing, calming, and heating treatment that helps reduce irritation and inflammation in skin. Green may be selected to promote an even complexion because green light balances out redness and blotches for naturally beautiful skin. Yellow may be selected to reduce redness because yellow light alleviates inflammation, sunburn, rosacea, and/or other skin conditions. Orange may be selected to enhance the user’s glow from withing because orange light revitalizes your skin for a brighter glow and adds radiance and vitality to dull skin. Finally, infrared light may be selected to penetrate deeper into the skin. Moreover, any combination of colors may be selected to tailor the treatment to the user’s needs.

A 432 Hz sound source is provided in the tent in FIG. 1.

In some implementations, the following example parameters are included for the sound source:

Signal-to-noise ratio. SPL: 60-70 DB.

Transducer: 1×40 mm.

Dimensions: (H×W×D) 141×94×42 (mm).

Weight: 184 g.

Control and Connection Specifications:

- Bluetooth version 4.2.
- Bluetooth transmitter power 0-9 dBm.
- Bluetooth transmitter frequency range 2.402-2.480 GHz.
- Bluetooth transmitter modulation GFSK, π/4 DQPSK, 8DPSK.

Combining specific sounds in/with music will be programmable and customized for specific therapeutic sessions. 432 Hz is the harmonic intonation of nature. Playing and listening to music that has been tuned to 432 Hz can make a listener's body, and the organic world which surrounds the body, resonate in a natural way. As a result, the listener may be filled with a sense of peace and well-being, regardless of the kind of song chosen. Providing music that has been tuned to the "scientific" 432 Hz frequency may benefit a listener, whereas listening to music tuned to the "disharmonic" 440 Hz frequency harms a listener by causing stress, negative behaviors, and unstable emotions. Listening to 432 Hz music resonates inside a body, releases emotional blockages, and expands consciousness.

Combining sound with steam and light within the hermetically sealed tent of the tent system enhances each variable's unique healing potential.

Figure 2:
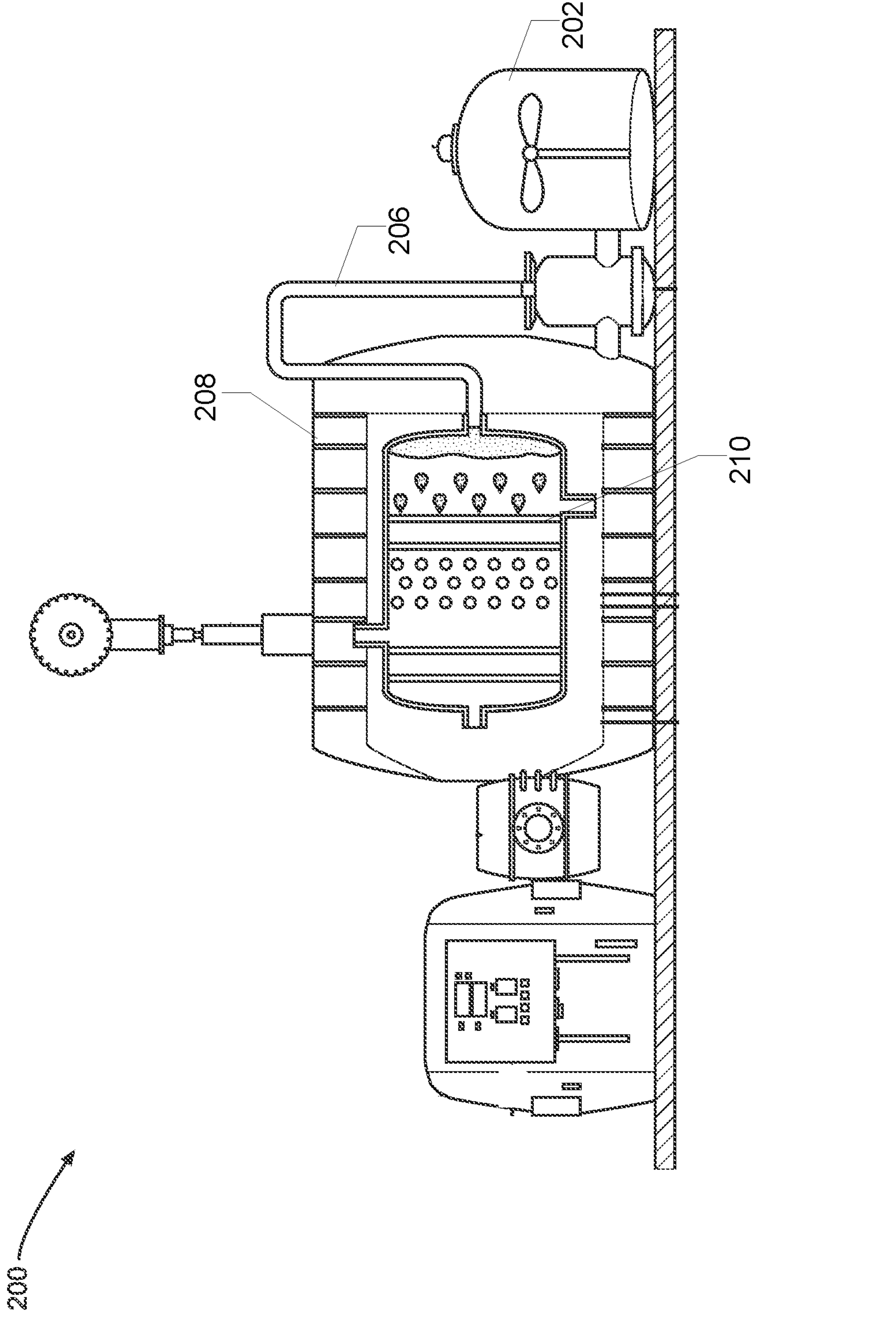
FIG. 2 illustrates a schematic diagram of a steam source in accordance with aspects in the present disclosure.

FIG. 2 illustrates a schematic diagram of a steam source 200 in accordance with aspects in the present disclosure. The steam source 200 shown in FIG. 2 includes a water tank 202 with a filter. The water may be placed in the water tank 202 and filtered through a water feed line 206 to a second water tank 208, which includes an external heater coil 210. Steam is created and moves into the tent 102.

Figure 3:
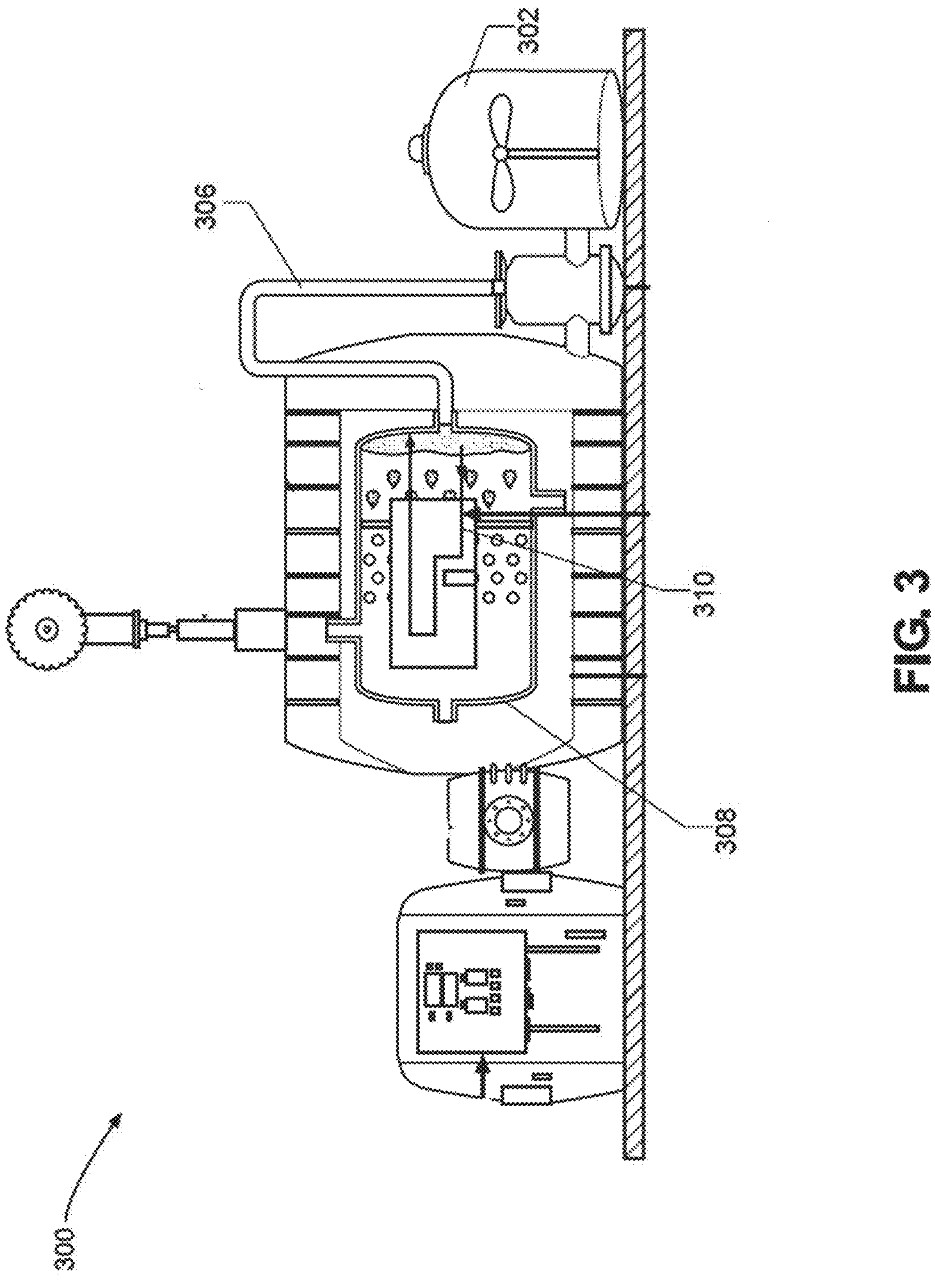
FIG. 3 illustrates another schematic diagram of a steam source in accordance with aspects in the present disclosure.

FIG. 3 illustrates a schematic diagram of a steam source 300 in accordance with aspects in the present disclosure. The steam source 300 shown in FIG. 3 includes a water tank 302 with a filter. The water may be placed in the water tank 302 and filtered through a water feed line 306 to a second water tank 308, which includes an internal heater coil 310. Steam is created and moves into the tent 102.

Figures 4A, 4B:
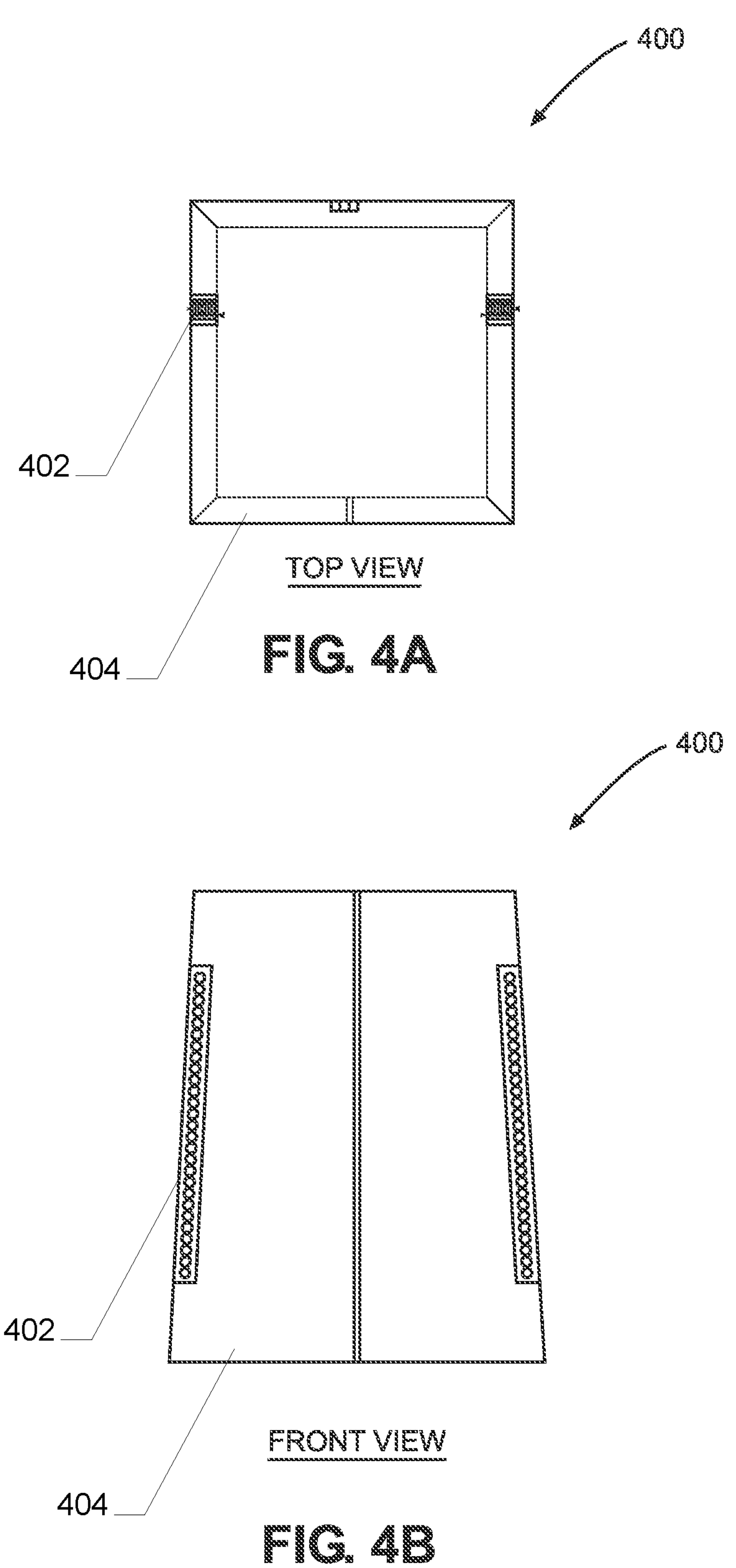
FIGS. 4A and 4B illustrate schematic diagrams of a top view and a front view of a tent system in accordance with aspects in the present disclosure.

FIGS. 4A and 4B illustrates schematic diagrams of a top view and a front view of a tent system 400 in accordance with aspects in the present disclosure. A light source 402 (LED lighting) is shown in a tent 404.

Figure 5A:
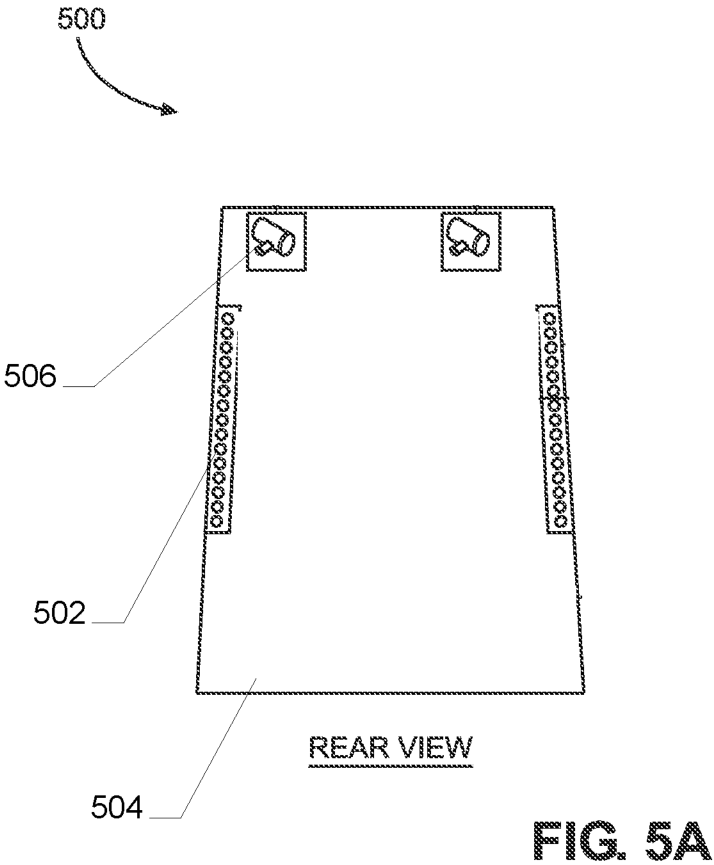
FIGS. 5A and 5B illustrate schematic diagrams of a rear view and an isometric view of a tent system in accordance with aspects in the present disclosure.
Figure 5B:
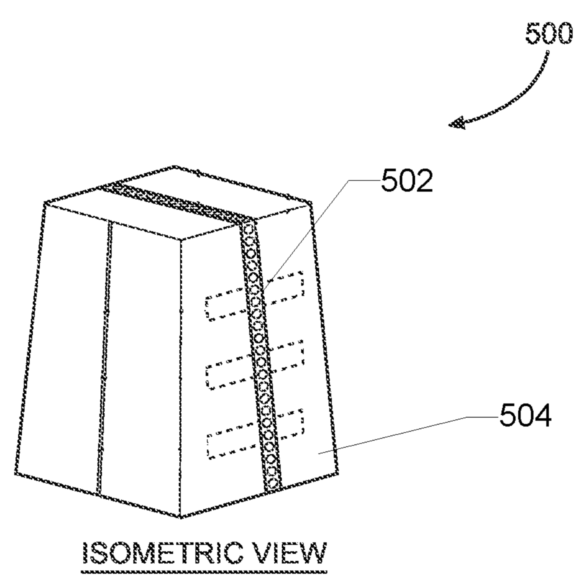

FIGS. 5A and 5B illustrates schematic diagrams of a rear view and an isometric view of a tent system 500 in accordance with aspects in the present disclosure. A light source 502 (LED lighting in a strip (4 w/3 k/55)) is shown in the tents 504, secured by Velcro fasteners. Stereo speakers 506 (A432) IP67/68 rated) are shown as part of a sound source.

Figures 6, 7:
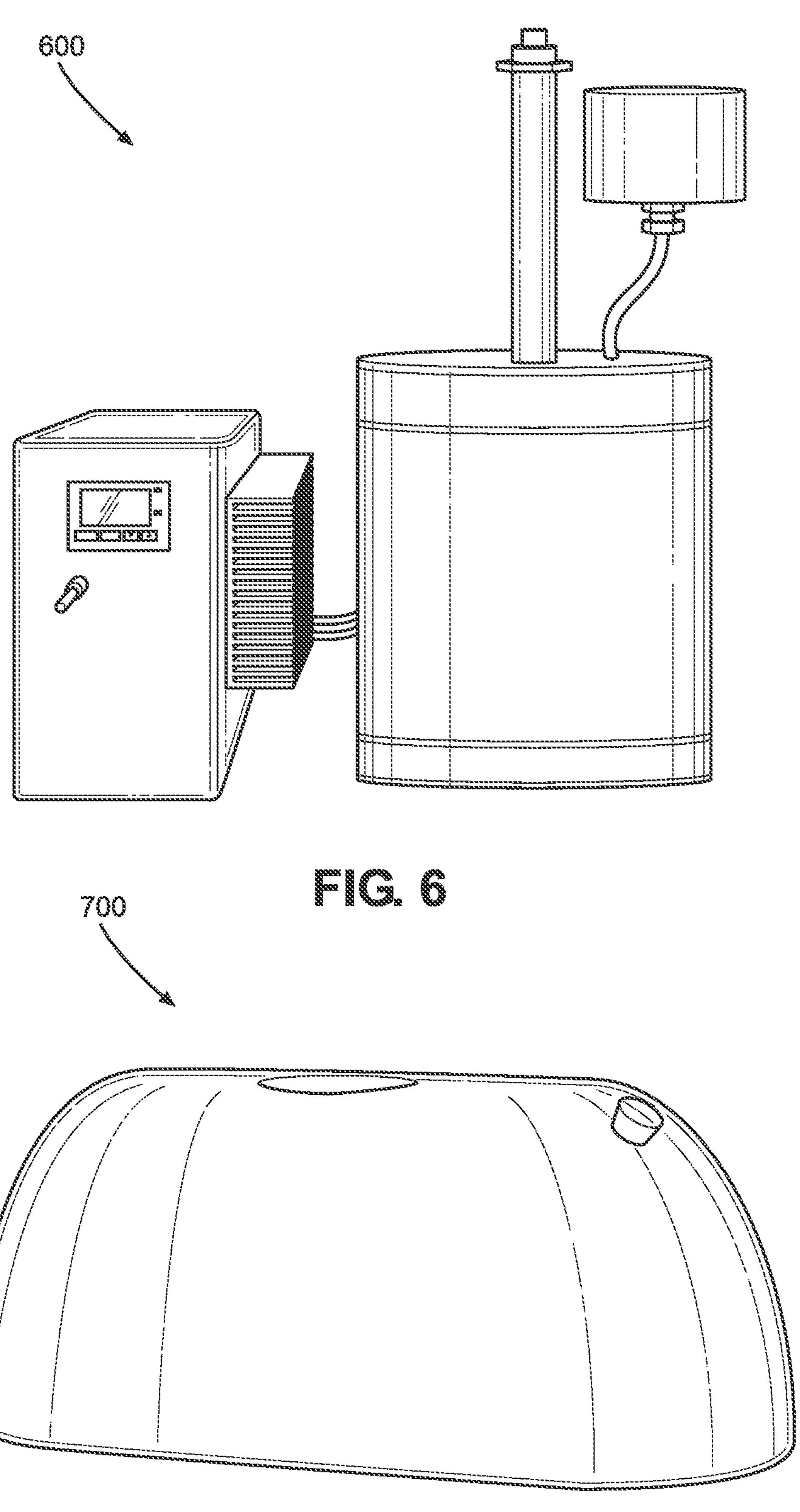
FIG. 6 is a perspective view of a steam source of a tent system in accordance with aspects in the present disclosure.
FIG. 7 illustrates a perspective view of a steam source of a tent system in accordance with aspects in the present disclosure.

FIG. 6 is a perspective view of a steam source 600 of a tent system in accordance with aspects in the present disclosure. The steam source 600 is adapted for one 110-watt outlet. In other implementations, the steam source 600 is adapted for two 110-watt outlets.

FIG. 7 illustrates an image of a steam source 700 of a tent system in accordance with aspects in the present disclosure. The steam source 700 is a steam unit shell concept design.

FIGS. 8A-C are schematic diagrams of a steam source 800 of a tent system in accordance with aspects in the present disclosure. The steam source 800 is a steam dispenser unit concept design including a steam intake 802, a removable dispenser overflow catch tray 804, and an adjustable direction steam output valve 806.

FIGS. 9A-C are perspective views of a steam source 900 of a tent system in accordance with aspects in the present disclosure.

FIG. 10 illustrates a schematic diagram of a steam source 1000 in accordance with aspects in the present disclosure. The steam source 1000 shown in FIG. 10 includes a water tank 1002 with a filter 1004. The water may be placed in the water tank 1002 and filtered through a water feed line 1006 to a second water tank 1008, which includes an internal heater coil 1010. Steam is created and moves into the tent.

FIG. 11 illustrates a schematic flow diagram of a control system 1100 in accordance with aspects in the present disclosure. The control system 1100 includes Bluetooth or other wireless technology for controlling the tent system, including the steam source, the light source, and the sound source. The control system 1100 may include at least Bluetooth version 4.2 having a transmission power of at least 0-9 dBm, a transmitter frequency range of at least 2.402-2.480 GHz, and a transmitter modulation of at least GFSK, π/4 DQPSK, and/or 8DPSK.

FIG. 12 is schematic diagrams of a steam source 1200 of a tent system in accordance with aspects in the present disclosure. The steam source 1200 is a contoured steam dispenser unit concept design including steam output valves 1202.

FIG. 13 is a flowchart of example operations 1300 of a method of using a tent system. An operation 1302 provided a hermetically sealed tent. An operation 1304 provides a steam source. An operation 1306 provides a light source. An operation 1308 provides a sound source. An operation 1310 places a user inside the hermetically sealed tent. An operation 1312 exposes the user to steam, light, and sound.

FIG. 14 is a flowchart of example operations 1400 of a method of treatment of a condition. An operation 1402 provides a hermetically sealed tent. In some implementations, the tent may be made of hemp or other materials capable of providing a hermetically sealed and anti-microbial environment.

The hermetically sealed tent includes a steam source, a light source, and a sound source. An operation 1404 provides determining a first predetermined administration of steam based on the condition. The first predetermined administration of steam may include a certain amount of steam to be administered to a tent system user. The first predetermined administration of steam may include a certain amount of time that the steam will be administered. The amount of steam and the amount of time the steam is provided may be based on the condition of the user.

An operation 1406 provides determining a second predetermined administration of light based on the condition. The second predetermined administration of steam may include the type of light administered and the amount of time the light is provided, which may or may not be the same amount of time as the steam or sound administration.

An operation 1408 provides determining a third predetermined administration of sound based on the condition. The third predetermined administration of sound may include the type of sound administered and the amount of time the sound is provided, which may or may not be the same amount of time as the steam or light administration.

For example, the setting of steam, light, and sound may be based on the following Tables 1 and 2:

TABLE 1

| PRESCRIPTION | SOUND | LIGHT | STEAM TIME | HEALTH BENEFITS |
|---|---|---|---|---|
| PRESCRIPTION 1 | A432-Binary Beats-A432@486 Hz | Red light-600 nm-700 nm | 10-15 Minutes | Increases alertness, memory & cognitive function, blood circulation to the skin and collagen production. Red Light: Infrared light (850 nm) and red light (660 nm): penetrates tissue to a depth of about 8-10 mm to help promote blood circulation and the relaxation of muscles, enhances immunity, stimulates metabolism, increases collagen production fivefold in the skin, triggering repair mechanism and stimulating fibroblast cells and cell growth. |
| PRESCRIPTION 2 | A432-Binary Beats-A432@306 Hz | Blue Light-415 nm to 470 nm | 15-20 Minutes | Stimulates upper dermal skin relief, minimizes scarring, reduces rashes, decreases depression |
| PRESCRIPTION 3 | A432-Binary Beats-A432@342 Hz | Green 252 nm | 15-20 Minutes | Reduces migraine headaches, pain, and the need for opioids-Calms and tightens skin |
| PRESCRIPTION 4 | A432-Binary Beats-A432@432 Hz | Orange 610 nm | 15-20 Minutes | Increases blood flow and metabolism |
| PRESCRIPTION 5 | A432-Binary Beats-A432@204 Hz | Yellow 590 nm | 15-20 Minutes | Fades dark spots, freckles and blemishes. Increases wound healing, collagen induction, skin hydration and the overall health of the skin |
| PRESCRIPTION 6 | A432-Binary Beats-A432@40 Hz | White 40 hz Flicker | 15-20 Minutes | Light and sound delivered at a certain frequency—40 flashes or clicks per second—appear to restart the natural 40 Hz gamma rhythm of the brain, improve the brain functions and diminish toxic levels of Alzheimer's-related proteins. Listening to a 40-Hz binaural beat for 20 minutes enhances working memory function. Gamma and beta oscillations are induced by 40-Hz binaural beats at the temporal and |

TABLE 1-continued

| PRESCRIPTION | SOUND | LIGHT | STEAM TIME | HEALTH BENEFITS |
|---|---|---|---|---|
| | | | | frontal regions. Emotional states of the participants have been known to change. |
| PRESCRIPTION 7 Combination LED Therapy | A432-Binary Beats-A432@486 Hz | Red light-600 nm-700 nm | | LED Red Light: Increases alertness, memory & cognitive function, increase blood circulation to skin) and Increases collagen production. Infrared light (850 nm) and red light (660 nm): penetrates tissue to a depth of about 8-10 mm to help promote blood circulation and the relaxation of muscles, enhances immunity, stimulates metabolism, increases collagen production fivefold in the skin, triggering repair mechanism and stimulating fibroblast cells and cell growth. |
| | 486 Hz A432-Binary Beats-A432@306 | Blue Light-415 nm to 470 nm | | Stimulates upper dermal skin relief, minimizes scarring, reduces rashes, decreases depression |
| PRESCRIPTION 8 Combination LED Therapy | A432-Binary Beats-A432@486 Hz | Red light-600 nm-700 nm | | LED Red Light: Increases alertness, memory & cognitive function, increase blood circulation to skin) and Increases collagen production. Infrared light (850 nm) and red light (660 nm): penetrates tissue to a depth of about 8-10 mm to help promote blood circulation and the relaxation of muscles, enhances immunity, stimulates metabolism, increases collagen production fivefold in the skin, triggering repair mechanism and stimulating fibroblast cells and cell growth. |
| | A432-Binary Beats-A432@342 Hz | Green 252 nm | 15-20 Minutes | Reduces migraine headaches, pain, and the need for opioids-Calms and tightens skin |

TABLE 2

| Frequency Hz | Tonal Key | Wave Frequency | Benefits | Spectrum Color | Copyrighted Music |
|---|---|---|---|---|---|
| A432 | D 324 Hz | Sine Wave | Decrease in depression | Blue Light-415 nm to 470 nm | All music and sounds are specifically designed, created and produced to target each individual and/or combination prescriptive approach. The combination of A432 Frequency, Pitch, and Binary beats will differ in range from 40 beats per min to 180 beats per min. The specific targeted utilization of instrumentation will treat the binary beats as a contrapuntal foundation to the accompanying rhythmical, melodic, and harmonic pattern. |
| A432 | F 342 Hz | Sine Wave | Migraine headaches, pain, opioids-Calms and tightens skin | Green 252 nm | |
| A432 | D 486 Hz | Sine Wave | Decrease in PTSD (Alertness, memory & cognitive function, skin) Increases blood flow and collagen production. | Red light-60 nm | |
| A432 | G 204 Hz | Sine Wave | Fades dark spots, freckles and blemishes, increases wound healing, collagen induction, skin hydration and the overall health of the skin | Yellow 590 nm | |
| A432 | A 432 Hz | Sine Wave | Increases blood flow and metabolism | Orange 610 nm | |

In some implementations, the tent system may not have one variable, such as light or sound. Once it is determined what steam, light, and/or sound will be provided in the tent system, an operation 1410 places a user inside the hermetically sealed tent for treatment. An operation 1412 administers the first predetermined administration of the steam to the user. An operation 1414 administers the second predetermined administration of the light to the user. An operation 1416 administers the third predetermined administration of the sound to the user. In some implementations, the determined second predetermined administration of the light is selected from LED/infrared light.

By way of example, in some implementations, red light may be selected if the condition includes at least one of muscle, immunological, metabolic, skin, and blood circulation conditions. In some implementations, blue light may be selected if the condition includes at least one of skin and fluid conditions. In some implementations, green light may be selected if the condition includes skin conditions. In some implementations, the third predetermined administration of the sound is providing sound at 432 Hz.

EXAMPLES

In order to illustrate the disclosure, the following examples are included. However, it is to be understood that these examples do not limit the disclosure and are only meant to suggest exemplary methods of practicing the disclosure.

In one example, the disclosed steam tent system was used to treat burns in a 2nd and 3rd-degree burn patient over a 60-day time period. The patient began the described treatment process after an initial waiting period of 5 days. Initially, there was some irritation of the skin of the burn patient, but the tissue responded positively after re-introducing LED light, steam, and A432 sound waves to the affected area in a hermetically sealed non-microbial controlled environment. The burn patient was also able to benefit from the detoxification of pain medication. The burn patient was able to focus on obtaining an overall feeling of well-being and reduced pain significantly with a matter of hours. This process allowed the skin and upper dermal areas to be more malleable for the regeneration process. The steam tent system increased the healing process of the burn patient by 40%.

This description provides examples, and is not intended to limit the scope, applicability or configuration of the principles described herein. Rather, the ensuing description will provide those skilled in the art with an enabling description for implementing various aspects of the principles described herein. As can be understood by one skilled in the art, various changes may be made in the function and arrangement of elements without departing from the application.

It should be appreciated by a person skilled in the art that one or more aspects of the disclosure may be implemented in a system to additionally or alternatively solve other problems than those described above. Furthermore, aspects of the disclosure may provide technical improvements to "conventional" systems or processes as described herein. However, the description only includes example technical improvements resulting from implementing aspects of the disclosure, and accordingly do not represent all technical improvements provided within the scope of the claims.

It should be noted that these methods describe examples of implementations, and that the operations and the steps may be rearranged or otherwise modified such that other implementations are possible. In some examples, aspects from two or more of the methods may be combined. For example, aspects of each of the methods may include steps or aspects of the other methods, or other steps or techniques described herein. Thus, aspects of the disclosure may provide for consumer preference.

The description set forth herein describes example configurations and does not represent all the examples that may be implemented or that are within the scope of the claims. The term "example" used herein means "serving as an exemplary, instance, or illustration," and not "preferred" or "advantageous over other examples." The detailed description includes specific details for the purpose of providing an understanding of the described techniques. These techniques, however, may be practiced without these specific details.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein but is to be accorded the broadest scope consistent with the principles and novel features disclosed herein.

The invention claimed is:

1. A tent system, comprising:

a hermetically sealed tent made of hemp and configured to provide an anti-microbial environment;

a steam source configured to supply an interior of the hermetically sealed tent with steam; and a light source configured to illuminate the hermetically sealed tent with light, wherein the steam and the light are configured in a predetermined combination to treat a user's condition.

2. The tent system of claim 1, wherein the steam source includes a water tank, water filler, pressurized steam generator, vaporizer, and overflow tank.

3. The tent system of claim 1, wherein the steam source provides the steam in a range of 105-120 degrees F.

4. The tent system of claim 1, wherein the light source is infrared.

5. The tent system of claim 1, further comprising:

a sound source.

6. The tent system of claim 5, wherein the sound source has a 432 Hz.

7. The tent system of claim 1, further comprising:

wireless technology to control at least one of the steam source, the light source, and the sound source.

8. The tent system of claim 1, wherein the tent system weighs less than 50 lbs.

9. The tent system of claim 1, further comprising:

a controller configured to select a prescription that specifies one or more parameter combinations of steam, light, and sound for one or more health benefits according to the condition.

10. A method for fabricating a tent system, comprising:

providing a hermetically sealed tent made of hemp and configured to provide an anti-microbial environment;

implementing a steam source into the hermetically sealed tent;

affixing at least one light source into the hermetically sealed tent; and providing a sound source to the hermetically sealed tent, wherein the steam source, the at least one light source, and the sound source are configured to provide a predetermined combination of steam, light, and sound based on a condition.

11. The method of claim 10, further comprising:

providing a controller configured to select a prescription that specifies one or more parameter combinations of steam, light, and sound for one or more health benefits according to the condition.

12. A method of using a tent system, comprising:

providing a hermetically sealed tent made of hemp and configured to provide an anti-microbial environment;

providing a steam source;

providing a light source;

providing a sound source; and placing a user inside the hermetically sealed tent; and exposing the user to a predetermined combination of steam, light, and sound based on a condition.

13. The method of claim 12, further comprising:

providing a controller configured to select a prescription that specifies one or more parameter combinations of steam, light, and sound for one or more health benefits according to the condition; and exposing the user to the steam, light, and sound based on the prescription.

14. A method of treatment of a condition comprising:

providing a hermetically sealed tent made of hemp and configured to provide an anti-microbial environment, the hermetically sealed tent including a steam source, a light source, and a sound source;

determining a first predetermined administration of steam based on the condition;

determining a second predetermined administration of light based on the condition;

determining a third predetermined administration of sound based on the condition;

placing a user inside the hermetically sealed tent;

administering the first predetermined administration of the steam to the user;

administering the second predetermined administration of the light to the user; and administering the third predetermined administration of the sound to the user.

15. The method of treatment of claim 14, wherein the determined second predetermined administration of the light is selected from infrared light.

16. The method of treatment of claim 14, wherein red light is selected if the condition includes at least one of muscle, immunological, metabolic, skin, and blood circulation conditions, wherein blue light is selected if the condition includes at least one of skin and fluid conditions, and wherein green light is selected if the condition includes skin conditions.

17. The method of treatment of claim 14, wherein the third predetermined administration of the sound is at 432 Hz.

18. The method of treatment of claim 14, wherein determining the first predetermined administration of steam, the second predetermined administration of light, and the third predetermined administration of sound based on the condition includes selecting, by a controller, a prescription that specifies one or more parameter combinations of steam, light, and sound for one or more health benefits.

19. The method of claim 14, further comprising:

providing a controller configured to select a prescription that specifies one or more parameter combinations of steam, light, and sound for one or more health benefits according to the condition; and exposing the user to the steam, light, and sound based on the prescription.

* * * * *